United States Patent [19]

Illig et al.

[11] Patent Number: 5,068,345

[45] Date of Patent: Nov. 26, 1991

[54] OXAZOLIDINONE ALDOL ADDUCT

[75] Inventors: Carl R. Illig; Alexander L. Weis, both of Rochester, N.Y.

[73] Assignee: Eastman Kodak Company, Rochester, N.Y.

[21] Appl. No.: 428,800

[22] Filed: Oct. 30, 1989

[51] Int. Cl.$^5$ .......................................... C07D 263/04
[52] U.S. Cl. .................................................... 548/230
[58] Field of Search ................................. 548/229, 230

[56]  References Cited

U.S. PATENT DOCUMENTS

| | | | |
|---|---|---|---|
| 4,487,963 | 12/1981 | Bock | 548/229 |
| 4,728,594 | 3/1988 | Nonogaki et al. | 548/228 |
| 4,940,797 | 7/1990 | Jones | 548/230 |
| 5,012,000 | 4/1991 | Illig et al. | 564/489 |

OTHER PUBLICATIONS

D. A. Evans, J. V. Nelson and T. R. Taber; Top. Stereochem., vol. 13, pp. 1–110 (1982).

"A Practical and Enantioselective Synthesis of Glycosphingolipids and Related Compounds. Total Synthesis of Globotriaosylceramide (Gb₃)", by K. C. Nicolaou et al., J. Am. Chem. Soc., vol. 110, pp. 7910–7912 (1988).

Kano et al., Jour. Org. Chem., vol. 54, pp. 513–515 (1989).

Royer et al., Jour. Org. Chem., vol. 44, pp. 3196–3201 (1979).

Kano et al., Chem. Pharm. Bull., vol. 37, pp. 2867–2869 (1989).

Kano et al., Chem. Pharm. Bull., vol. 36, pp. 3341–3347 (1988).

*Primary Examiner*—Donald G. Daus
*Attorney, Agent, or Firm*—Betty J. Deaton; J. Jeffrey Hawley

[57]  ABSTRACT

A oxazolidinone aldol adduct having the formula:

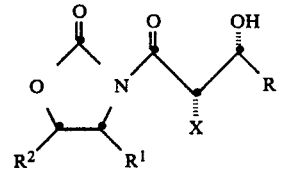

wherein R is alkyl having 6 or more carbons or aryl; $R^1$ is alkyl or aryl; $R^2$ is alkyl, aryl or hydrogen; and X is a halogen atom or an azide. This aldol adduct is useful in a process for making 2-amino-1,3 diols.

7 Claims, No Drawings

OXAZOLIDINONE ALDOL ADDUCT

FIELD OF THE INVENTION

This invention relates to an oxazolidinone aldol adduct useful for a process for making chiral 2-amino-1,3-diols as disclosed in commonly owned U.S. Ser. No. 428,799 filed on even date herewith by Carl R. Illig and Alexander L. Weis and entitled "Total Synthesis of Chiral 2-Amino-1,3-Diols", now U.S. Pat. No. 5,012,000.

BACKGROUND OF THE INVENTION

Glycosphingolipids and gangliosides are of crucial importance as major membrane constituents of the cell, the majority of which are located at the outer leaflet of the plasma membrane. Recent investigations have demonstrated that glycosphingolipids on cell surfaces are one important way in which nature expresses its individuality.

For example, they serve as specific markers of the cells, particularly those forming blood group antigens, tumor cell markers, cell adhesion organ specific markers and growth regulators. They have been also implicated as receptors for toxins, hormones and interferons.

It has been shown that sphingosine and its derivatives have a prominent intracellular regulatory function. However, the complete biological and pharmacological function of sphingosine still remains to be elucidated. Therefore, the development of an efficient stereoselective route to this material and its diastereomers on a multigram scale is still an important synthetic goal.

The important structural features of natural D-(+)-erythro-sphingosine include the absolute configuration at the two chiral centers of this aminodiol (2S, 3R) and the trans geometry of the double bond.

The process described in commonly owned U.S. Ser. No. 428,799 filed on even date herewith by Carl R. Illig and Alexander L. Weis and entitled "Total Synthesis of Chiral 2-Amino-1,3-Diols" is an efficient stereoselective route to the synthesis of 2-amino-1,3-diols, including sphingosine. It combines the advantages of less expense, exclusively chiral product, good overall yield and safety of reagents.

The oxazolidinone aldol adduct formed during this process is the subject of the present invention and is useful for synthesizing 2-amino-1,3-diols.

To further understand the nature of this invention, a reaction scheme is provided herein below. The oxazolidinone aldol adduct of the invention is produced in step A as shown.

oxazolidinone 1) enolize
2) OHC—CH=CH—$C_{13}H_{27}$     Step A → aldehyde aldol condensation product

Other compounds of the invention are made by conversion of the chloride to the azide as follows.

SUMMARY OF THE INVENTION

We have developed an oxazolidinone aldol adduct useful in a process for the preparation of chiral 2-amino-1,3-diols that is useful in the synthesis of 2-amino-1,3-diols.

More specifically, in accordance with the invention, there is provided a compound having the following formula:

wherein R is alkyl, having 6 or more carbons or aryl, $R^1$ is alkyl or aryl, $R^2$ is alkyl, aryl or hydrogen, and X is a halogen atom or an azide.

In a preferred embodiment of the invention, there is provided a compound having the above formula:

wherein R is —CH=CH(CH$_2$)$_{12}$CH$_3$, $R^1$ is benzyl, $R^2$ is hydrogen, and X is a halogen atom.

It is an advantageous feature of the invention that the oxazolidinone aldol adduct can be converted directly into the corresponding azido derivative without the need for protection of the hydroxyl group.

It is another advantageous feature of the invention that it is useful in a process for making 2-amino-1,3-diols, including D-erythro-sphingosine.

Advantageous features other than those noted hereinabove will become apparent upon reference to the following Description of Preferred Embodiments.

DESCRIPTION OF THE PREFERRED EMBODIMENTS

The compounds of the present invention are useful in a process for the preparation of chiral 2-amino-1,3-diols comprising four steps, two steps of which are shown as follows:

A. Performing an aldol condensation of a 3-haloacetylated chiral oxazolidinone with an aldehyde using conditions which preserve the chirality of the resulting aldol condensation product.

This 3-haloacetylated chiral oxazolidinone is prepared by the haloacetylation of commercially available (S)-4-benzyl-2-oxazolidinone with haloacetyl halide or haloacetic anhydride. The halogen becomes the leaving group, X, and the preferred halogen is bromine which produces greater yields. However, chlorine, fluorine and iodine can also be used.

In this step, a compound (oxazolidinone aldol adduct) is formed which has the following formula:

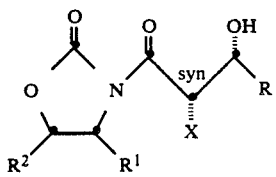

wherein R is selected from alkyl having 6 or more carbons or aryl. R can be ethyl, propyl, isopropyl, butyl, hexyl, nonyl, hexadecyl, vinyl, propenyl, decenyl, pentadecenyl, phenyl, naphthyl, anthryl, benzyl, phenethyl, tolyl, xylyl, etc. $R^1$ is alkyl or aryl. $R^1$ can be methyl, propyl, isopropyl, t-butyl, hexyl, isononyl, phenyl, benzyl, phenethyl, etc. $R^2$ is alkyl, aryl or hydrogen. $R^2$ can be methyl, propyl, isopropyl, t-butyl, hexyl, isononyl, phenyl, benzyl, phenethyl, hydrogen, etc. X is a halogen atom such as bromine, chlorine, iodine or fluorine or an azide.

In a preferred embodiment, the aldol condensation is performed with a 3-bromoacetyl-4-substituted chiral oxazolidinone and trans-2-hexadecenal. The preferred product is (S)-4-Benzyl-3-trans-2-bromo-3-hydroxy-4-octadecenoyl-2-oxazolidinone.

An example of the use of a chiral 3-haloacetyl-oxazolidinone to make amino acids is disclosed by D. A. Evans, E. B. Sjogren, A. E. Weber and R. E. Conn in "Asymmetric Synthesis of Anti-β-Hydroxy-α-Amino Acids," Tetrahedron Letters, Volume 28, pages 39–42 (1987).

An example of the use of a chiral 3-chloroacetyl oxazolidinone to make other derivatives which are in turn used to make amino acids is disclosed by D. A. Evans and Ann E. Weber in "Asymmetric Glycine Enolate Aldol Reactions: Synthesis of Cyclosporine's Unusual Amino Acids, MeBmt," J. Am. Chem. Soc., Volume 108, pages 6757–6761(1986).

Although any aldehyde can be used, an alkene aldehyde is preferable in order to make sphingosine. Examples of alkene aldehydes are trans-2-hexadecenal (trans-hexadec-2-en-1-al) and crotonaldehyde. Examples of useful saturated aldehydes used to make 2-amino-1-3-diols are listed in "Metal-Assisted Aldol Condensation of Chiral alpha-Halogenated Chiral Epoxide Synthesis," J. Am. Chem. Soc., Vol. 108, pages 4595–4602(1986).

Generally, proportions of reagents can vary over a wide range. It is preferred to use greater than one equivalent of the 3-haloacetylated oxazolidinone relative to the aldehyde(1.0–1.5 equivalency).

Conditions which preserve the chirality, i.e., syn-stereochemistry, of the resulting aldol condensation product include use of a tin trifluoromethanesulfonate, or a boron trifluoromethanesulfonate and use of a mild peroxide solution to oxidize the boron such as 30% hydrogen peroxide solution. The use of dibutylboron trifluoromethanesulfonate is preferred. This step is critical in that it must preserve the chiral structure in the resulting aldol condensation product. It is also necessary to avoid strongly basic or acidic reagents or conditions as well as temperatures greater than 20 degrees Celsius. These can result in sideproducts including products resulting from loss of water, somerization at the chiral center substituted by halogen, epoxide formation from loss of HX, where X is a halogen, or products from a retro-aldol reaction.

B. Treating the aldol condensation product with an alkali metal azide. The preferred alkali metal azide is sodium azide. Alternatively, other azide salts can be used including, but not limited to, lithium azide, potassium azide, cesium azide or a tetraalkylammonium azide. Polar aprotic solvents such as dimethyl sulfoxide are preferred. This step replaces the active halogen with an azido substituent from the sodium azide producing mostly anti product. Isolation of the predominant anti product occurs, i.e., the chiral product.

The amount of azide present must be greater than 1 gram equivalent. The temperature ranges from −78° C. to 100° C. The pH is preferably ≦10 for reactions run in water. Any solvent in which the azide reagent is soluble, but which does not react with the aldol product, can be used. Dimethyl sulfoxide(DMSO) is preferred.

The thus produced intermediates of steps A and B above can be used to make 2-amino-1,3-diols such as D-erythro-sphingosine as disclosed in the Illig and Weis application U.S. Ser. No. 428,799 mentioned above.

Examples of aldehydes which can be used as the starting material for making the compounds of the invention include:

o-Anisaldehyde, 9-Anthraldehyde, Benzaldehyde,
p-Bromobenzaldehyde, p-Butoxybenzaldehyde,
o-Chlorobenzaldehyde, 2-Chloro-5-nitrobenzaldehyde, 5-Chloro-2-thiophenecarboxaldehyde,
p-Cyanobenzaldehyde, p-Diethylaminobenzaldehyde, 2,5-Dimethoxybenzaldehyde, 3,4-Dimethoxybenzaldehyde,
p-Dimethylaminobenzaldehyde, 3,5-Dimethyl-1-phenylpyrazole-4-carboxaldehyde,
p-Ethylbenzaldehyde, Furfural, p-Hexylbenzaldehyde,
p-Hexyloxybenzaldehyde, 1-Naphthaldehyde, m-Nitrobenzaldehyde, o-Nitrobenzaldehyde,
p-Nitrobenzaldehyde, p-Octylbenzaldehyde,
p-Octyloxybenzaldehyde, Piperonal,
p-Propylbenzaldehyde, 2-Thiophenecarboxaldehyde and
p-Tolualdehyde.

The aldehydes are commercially available, for example, from Aldrich Chemical Co., Inc., Sigma Chemical Co., and Eastman Kodak Co. Also, there are many well-known methods of preparing trans-α,β-unsaturated aldehydes. The aldehyde needed to make sphingosine is not available commercially but can be prepared by the method of Ito(Y. Ito, M. Sawayara and T. Hayashi, Tetrahedron Letters, 29, 239(1988). The aldehydes, including trans-2-hexadecenal useful for making sphingosine, can also be more conveniently prepared by the following steps.

A. Preparation of a reagent of the structure:

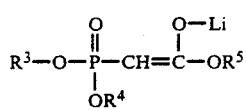

where each $R^3$, $R^4$ and $R^5$ independently is alkyl or aryl such as methyl, ethyl, propyl, benzyl, phenyl, etc., by reaction, i.e., lithiation of a trisubstituted phosphonoacetate with lithium halide in the presence of a base in a dry organic solvent. A trisubstituted phosphonoacetate has the formula:

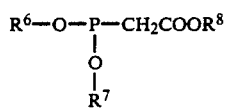

wherein $R^6$, $R^7$ and $R^8$ independently is alkyl or aryl such as methyl, ethyl, propyl, benzyl, phenyl, etc. The solvent used may be any of a number of dry organic solvents including tetrahydrofuran, dioxane and diethyl ether. A dry organic solvent is generally defined as a solvent that has been treated with a drying agent such as $CaCl_2$ or $MgSO_4$ to remove as much water as possible, or distilled from drying agents such as sodium metal, or sodium or calcium hydride. This term is well known in the art. The preferred solvent is tetrahydrofuran. The preferred base is 1,8-diazabicyclo[5.4.0]-undec-7-ene. Alternatively, other bases can be used including any trialkylamine.

Lithium chloride is the preferred lithiating agent. Alternatively, the lithium halide used can be lithium iodide, lithium fluoride or lithium bromide.

B. Condensation of the reagent of step A with tetradecenal is performed to produce the ester of an $\alpha,\beta$-unsaturated carboxylic acid. As stated previously, tetradecenal is the most preferred aldehyde since the product is required to produce sphingosine. However, other aldehydes can be used to produce 2-amino-1,3-diols.

C. Reducing the $\alpha,\beta$-unsaturated carboxylic acid ester to the 2-unsaturated alcohol under conditions such that the double bond is preserved. The conditions refer to strength of the reducing agent. Diisobutylaluminum hydride is preferred. Lithium borohydride or lithium aluminum hydride could also be used.

Conditions are also used which successfully reduce the ester group without also reducing the unsaturated $>C=C<$ and azide groups. Such conditions are well known in the art and are reviewed by J. March in "Advanced Organic Chemistry" 3rd Edition, John Wiley and Sons, New York, N.Y. (1985) beginning at page 1093. (Note particularly Table 5 which provides the reactivity of various functional groups with various metal hydrides and catalytic hydrogenation, and page 1107 relating to the reduction of esters).

D. Oxidizing the 2-unsaturated alcohol to the aldehyde. Pyridinum dichromate is the preferred oxidizing reagent. Alternatively, pyridinium, chlorochromate or Moffat-type oxidation reagents including oxalyl chloride-dimethyl sulfoxide, pyridine-sulfur trioxide-dimethylsulfoxide and trifluoroacetic anhydride-dimethylsulfoxide may be used.

EXAMPLE 1

Melting points were determined with a melting point apparatus and are uncorrected. Infrared spectra were recorded on a spectrophotometer. Optical rotations were determined on a polarimeter in a jacketed cell (equipped with a constant temperature bath) at 589 nm (sodium D line). $^1H$ NMR spectra were recorded on a spectrometer. Chemical shifts are reported in ppm from tetramethylsilane on the $\delta$ scale with residual solvent as the internal standard (chloroform 7.26 ppm). Data are reported as follows: chemical shift, multiplicity (s = singlet, d = doublet, t = triplet, q = quartet, m = multiplet, and br = broad), integration, coupling constant (Hz), and interpretation.

Analytical thin layer chromatography (TLC) was performed using 0.25 mm silica gel plates visualized by UV fluorescence and by an aqueous ceric ammonium molybdate spray followed by heat. Routine liquid (flash) chromatography was performed on 32-63 $\mu m$ silica gel with the indicated solvent system. The solvent system used to prepare the column, if different, is reported separately.

When necessary, solvents and reagents were dried prior to use. Diethyl ether and tetrahydrofuran were distilled from sodium metal/benzophenone ketyl. Toluene was distilled from sodium metal. Dichloromethane, and triethylamine were distilled from calcium hydride under an argon atmosphere. Nonaqueous titration grade N,N-dimethylformamide was stored over activated 4 Å molecular sieves under an inert (argon) atmosphere. Reagent grade pyridine was stored over potassium hydroxide under an inert (argon) atmosphere.

Anhydrous acetonitrile, anhydrous dimethyl sulfoxide, diisobutylaluminum hydride in toluene, and (S)-(−)-4-benzyl-2-oxazolidinone were obtained from Aldrich Chemical Co.

(S)-3-bromoacetyl-4-benzyl-2-oxazolidinone and S-3-chloroacetyl-4-benzyl-2-oxazolidinone were prepared by the procedures of A. Abdel-Magid, L. N. Pridgen, D. S. Eggleston, and I. Lantos as described in *Metal-Assisted Aldol Condensation of Chiral $\alpha$-Halogenated Imide Enolates: A Stereocontrolled Chiral Epoxide Synthesis*, J. Am. Chem. Soc. 108, 4595–4602 (1986).

Anhydrous lithium chloride was prepared by drying the finely powdered salt at 300° C. for 5 h.

Moisture sensitive reactions were carried out under an atmosphere of argon using oven-dried glassware. All solutions were magnetically stirred unless otherwise indicated.

Trans-Ethyl 2-Hexadecenoate

To a solution of 18.8 g (0.443 mol) of anhydrous lithium chloride in 1200 mL of dry acetonitrile and 600 mL of dry tetrahydrofuran was added 99.3 g (0.369 mol) of triethyl phosphonoacetate followed by 55.2 mL (0.369 mol) of 1,8-diazabicyclo-[5.4.0]undec-7-ene. After 5 min at 25° C., 98.0 g (0.369 mol based on 80% purity) of technical grade tetradecanal in 600 mL of tetrahydrofuran was added. After stirring for 1.5 h, the mixture was poured into 16 L of water and extracted with 3×2.5 L of technical grade diethyl ether. The combined organic extracts were washed with 4 L saturated aqueous sodium bisulfite to remove unreacted aldehyde, then with 2 L of brine and dried over sodium sulfate. The solution was concentrated to a milky oil and placed under vacuum (0.5 torr/4 h) to afford 140 g of an oily white suspension. The mixture was fractionally distilled collecting a small amount of tetradecenal (104°–107° C./0.45 torr then 128°–137° C./0.25 torr) followed by 98.1 g (94%) of pure trans-ethyl 2-hexadecenoate (137°–142° C./0.25 torr) as a colorless mobile oil.

IR (thin film) 2920, 2850, 1725, 1465, 1265, 1175, 1045 cm$^{-1}$; $^1$H NMR (CDCl$_3$, 300 MHz) δ7.00 (dt, 1, J=15.5, 6.8 Hz, CH$_2$CH=), 5.84 (dt, 1, J=15.5, 1.2 Hz, COCH=), 4.21 (dd, 2, J=14.2, 7.2 Hz, CH$_2$O), 2.23 (qd, 2, J=6.9, 1.2 Hz, CH$_2$CH=), 1.49 (t, 2, J=7 Hz, CH$_2$CH$_2$CH$_3$), 1.3 (m, 20, CH$_2$CH$_2$CH$_2$), 0.92 (t, 3, J=7 Hz, CH$_2$CH$_2$CH$_3$). R$_f$(5% ethyl acetate:hexanes):tetradecanal, 0.29; ester product, 0.31. MS (FD): m/e 282 (M+).

Trans-2-hexadecenol

To a cooled (0° C.) solution of 35.1 g (0.124 mol) of trans-ethyl 2-hexadecenoate in 100 mL of dry toluene was added 298 mL (0.298 mol) of a 1.0M solution of diisobutylaluminum hydride in toluene over ca. 6 min. After stirring for 45 min, the mixture was carefully quenched with 20 mL of absolute methanol. The mixture was poured into 1.5 L of 0.5M sodium potassium tartrate and mechanically stirred vigorously for 5 h. After standing undisturbed for 14 h, the mixture was filtered through diatomaceous earth, referred to hereinafter as Celite, (the Celite is moistened with a solvent and poured onto a filter paper in a Buchner funnel under vacuum to form a pad of the Celite over the paper), the layers separated and the aqueous layer extracted with 100 mL ethyl acetate. The combined organic layers were dried over sodium sulfate and concentrated to afford 29.5 g (99%) of a soft, waxy white solid. This material was used directly in the following reaction.

IR (thin film) 3000–3500, 2920, 2850, 1420, 970 cm$^{-1}$; $^1$H NMR (CDCl$_3$, 300 MHz) δ5.6–5.8 (m, 2, CH=CH), 4.11 (d, 2, J=4.9 Hz, CH$_2$OH), 2.04 (q, 2, J=6.4 Hz, CH$_2$CH=), 1.0–1.3 (m, 22, CH$_2$), 0.91 (t, 3, J=7 Hz). R$_f$(15% methanol:dichloromethane):trans-ethyl 2-hexadecenoate, 0.60; trans-2-hexadecenol, 0.17.

Trans-2-hexadecenal

To a stirred suspension of 60.6 g (0.161 mol) pyridinium dichromate in 100 mL of dichloromethane was added 25.7 g (0.107 mol) of trans-2-hexadecenol. After 4 h at 25° C., the mixture was filtered (through Celite diatomaceous earth) and the resulting brown solution refiltered through Florisil, an activated magnesium silicate in the form of hard, porous, stable, white granules that are free from dusting sold by Floridin Co. The colorless solution obtained was concentrated in vacuo to 21.8 g (86%) of a white solid. Distillation (90°–100° C./0.40–0.45 torr) provided 19.1 g (75%) of pure trans-2-hexadecenal as a white waxy solid. IR (thin film as melt) 2920, 2850, 1695, 1465, 975 cm$^{-1}$; $^1$H NMR (CDCl$_3$, 300 MHz) δ9.53 (d, 1, J=6.7 Hz, CHO), 6.88 (overlapping dt, 1, J=15.7, 6.7 Hz, OHCCH=), 1.53 (m, 2, CH$_2$CH$_3$), 1.1–1.2 (m, 20, CH$_2$CH$_2$CH$_3$), 0.90 (t, 3, J=7 Hz, CH$_2$CH$_3$). R$_f$(15% ethyl acetate:hexanes):trans-2-hexadecenol, 0.19 trans-2-hexadecenal, 0.44. MS(FD) m/e 238 (M+).

Aldol Adduct
(S)-4-Benzyl-3-(trans-2-chloro-3-hydroxy-4-octadecenoyl)-2-oxazolidinone from (S)-4-Benzyl-3-bromoacetyl-2-oxazolidinone To a flame-dried flask under argon was added 2.481 g (9.780 mmol) of (S)-3-chloroacetyl-4-benzyl-2-oxazolidinone and the flask was reflushed with argon to exclude all traces of oxygen. 300 mL of dry oxygen-free diethyl ether (freshly distilled from sodium/benzophenone ketyl under argon) was added and the resulting solution cooled over 5 min to −35° C. (internal temperature). The freshly distilled oxygen-free triethylamine (2.30 mL, 16.5 mmol) was added. Cooling was continued and immediately upon reaching an internal temperature of −50° C. (to prevent crystallization of the dissolved imide), 10.8 mL (10.8 mmol) of a 1.0M solution of dibutylboron triflate in dichloromethane was added dropwise over 3 min (maintaining the temperature at −50°±2° C.). The pale yellow solution was stirred 15 min at −50° C., warmed to 20° C. over ca. 45 min and stirred at 20° C. for 30 min. (Triethylamine hydrotriflate precipitated as a white solid becoming an oil above 0° C.) The solution was recooled to −65° C. (internal temperature) and 1.667 g (6.990 mmol) of trans-2-hexadecenal in 20 mL of dry, oxygen-free diethyl ether was added by cannula. After stirring at −65° C. for 15 min, the solution was warmed to 0° C. over 1.5 h, stirred at 0° C. for 30 min and the cooling bath was removed. Thin layer chromatography analysis during this time indicated the disappearance of all but 5–10% of the starting aldehyde. After stirring an additional 30 min, the internal temperature had reached 20° C. Ethyl acetate (200 mL) was added and the solution washed with 2×150 mL of 0.5M aqueous sodium bisulfate, 200 mL of brine and dried over anhydrous sodium sulfate. The solution was then concentrated in vacuo to 5.9 g of a pale amber oil which was redissolved in 50 mL of diethyl ether. The 30% hydrogen peroxide (15 mL) was added followed by sufficient absolute ethanol to obtain a homogeneous solution (ca. 50 mL). After stirring at 20° C. for 14 h, the mixture was concentrated in vacuo without warming (bath temperature≦20° C.) to ca. 20% volume to remove the majority of the solvents. Ethyl acetate:hexane (1:1 200 mL) was added and the solution washed with 100 mL of water, 100 mL of saturated aqueous sodium bicarbonate, brine and dried over anhydrous sodium sulfate. Concentration in vacuo (≦20° C.) afforded 4.7 g of a colorless resin. The mixture was flash chromatographed on 400 g of silica gel eluting with a gradient of 4% ethyl acetate in dichloromethane:hexanes (40:60) to 6% ethyl acetate in dichloromethane:hexanes (60:40) over ca. 4 L. First eluted was 98 mg (5.9%) unreacted trans-2-hexadecenal followed by the unreacted excess imide (mixed with a minor diastereomeric aldol product) followed by 2.082 g (61%) of the desired aldol adduct as a nearly colorless resin (64% based on recovered aldehyde): [α]$_D^{20}$+52.7° C. (c 1.3, CH$_2$Cl$_2$); IR (thin film) 3200–3600, 2920, 2850, 1780, 1710, 1390, 1210, 1110, 900 cm$^{-1}$; $^1$H NMR (CDCl$_3$, 300 MHz) δ7.2–7.4 (m, 5, Ph), 5.89 (dt, 1, J=15.5, 6.8 Hz, CHCH=), 5.74 (d, 1, J=5.0 Hz, CHCl), 5.55 (dd, 1, J=15.5, 6.6 Hz, CH$_2$CH=), 4.72 (m, 1, NCH), 4.64 (br t, 1, J=5.3 Hz, CHOH), 4.27 (d, 2, J=7.3 Hz, CH$_2$O), 3.35 (dd, 1, J=13.4, 3.3 Hz, CH$_2$Ph), 2.87 (dd, 1, J=13.4, 9.4 Hz, CH$_2$Ph), 2.73 (br s, 1, OH), 2.08 (dd, 2, J=13.8, 6.8 Hz, CH$_2$CH=), 1.05–1.25 (m, 22, CH$_2$), 0.91 (t, 3, J=6 Hz, CH$_3$). R$_f$(4% ethyl acetate:dichloromethane):trans-2-hexadecenal, 0.66; imide, 0.60; minor aldol diastereomer, 0.53; major aldol diastereomer adduct product, 0.45.

(S)-3-(Trans-2-azido-3-hydroxy-4-octadecenoyl)-4-benzyl-2-oxazolidinone from
(S)-4-Benzyl-3-(trans-2-chloro-3-hydroxy-4-octadecenoyl)-2-oxazolidinone To 1.21 g (2.46 mmol) of the aldol adduct and 351 mg (5.4 mmol) of sodium azide was added 12.0 mL of dry N,N-dimethylformamide and warmed to 40°-45° C. until TLC analysis (25% ethyl acetate:hexanes) indicated that ca. 5% trans-2-hexadecenal (from retroaldol reaction) was present, at which point the displacement was ≧95% complete (3.0-4.5 h). (Monitoring by disappearance of starting aldol adduct was difficult due to its co-elution on TLC with the azide product minor diastereomer). The mixture was partitioned between 200 mL of ethyl acetate:hexanes (1:1) and 200 mL of water. The aqueous layer was extracted with 50 mL of ethyl acetate:hexanes (1:1) and the combined organic layers washed with 3×100 mL water (emulsions broken by addition of brine), 100 mL of brine and dried over anhydrous sodium sulfate. Concentration in vacuo afforded 1.19 g of a yellow oil which $^1$H NMR spectral analysis revealed to contain an 86:14 mixture of azide epimers A and B, respectively, along with small amounts (<10%) of products from the retroaldol reaction. Flash chromatography on 150 g silica gel (20% ethyl acetate:hexanes) provided 27.5 mg (4.7%) of trans-2-hexadecenal followed by 0.822 g (67%) of the pure azide product (epimer A) as a colorless oil. Last eluted was 164 mg of a mixture of a minor azide epimer B and 3-azidoacetyl-4-benzyl-2-oxazolidinone (the result of an azide displacement on the retroaldol product 3-chloroacetyl-4-benzyl-2-oxazolidinone) followed by 70 mg of a colorless oil consistent, by $^1$H NMR, with the pure minor azide diastereomer B. Data for the product, diastereomer A: $[\alpha]_D^{20}$ +26.8° (c 1.1, $CH_2Cl_2$); IR (thin film) 3250-3600, 2920, 2850, 2110, 1780, 1705, 1390, 1210, 1115, 700 $cm^{-1}$; $^1$H NMR ($CDCl_3$, 300 MHz) δ7.1-7.2 (m, 5, Ph), 5.93 (overlapping dt, 1, J=15.4, 6.7 Hz, OC—CH═), 5.62 (dd, 1, J=15.4, 7.3 Hz, $CH_2CH$═), 5.08 (d, 1, J=7.7 Hz, $CHN_3$), 4.73 (m, 1, NCH), 4.52 (q, 1, J=6.9 Hz, CHOH), 4.23 (m, 2, $CH_2O$), 3.32 (dd, 1, J=13.5, 3.4 Hz, $CH_2Ph$), 2.76 (dd, 1, J=13.5, 9.7 Hz $CH_2PH$═), 2.44 (d, 1, J=7.0 Hz, OH) 2.10 (q, 2, J=6.9 Hz, $CH_2CH$═), 1.1-1.5 (m, 22, $CH_2$), 0.88 (t, 3, J=7 Hz, $CH_3$). $R_f$ (25% ethyl acetate:hexanes): starting aldol adduct, 0.20; major azide product epimer A, 0.33; minor azide epimer B, 0.20; trans-2-hexadecenal, 0.90.

EXAMPLE 2

Aldol Adduct
(S)-4-Benzyl-3-(trans-2-bromo-3-hydroxy-4-octadecenoyl)-2-oxazolidinone from
(S)-3-Bromoacetyl-4-benzyl-2-oxazolidinone To an oven-dried flask under argon in a dry box was added 2.97 g (9.98 mmol) of (S)-3-bromoacetyl-4-benzyl-2-oxazolidinone, and the flask was reflushed with argon to exclude all traces of oxygen. 300 mL of dry oxygen-free diethyl ether (freshly distilled from sodium/benzophenone ketyl under argon) was transferred by cannula into the flask, and the resulting solution cooled over 5 min. to −35° C. (internal temperature). The freshly distilled oxygen-free triethylamine (2.30 mL, 16.5 mmol) was added. Cooling was continued and, upon reaching an internal temperature of −78° C., 10.8 mL (10.8 mmol) of a 1.0M solution of dibutylboron triflate in dichloromethane was added dropwise over 3 min. The pale yellow solution was stirred 15 min. at −78° C., warmed to 20° C. over ca. 45 min. and stirred at 20° C. for 30 min. (Triethylamine hydrotriflate precipitated as a white solid becoming an oil above 0° C.) The solution was recooled to −65° C. (internal temperature), and 1.67 g (6.99 mmol) of trans-2-hexadecenal in 20 mL of dry, oxygen-free diethyl ether was added by cannula. After stirring at −65° C. for 15 min., the solution was warmed to 0° C. over 0.5 h, stirred at 0° C. for 40 min., and the cooling bath was removed. TLC analysis during this time indicated the disappearance of all of the starting aldehyde. After stirring an addition 30 min., the internal temperature had reached 20° C. Ethyl acetate (200 mL) was added, and the solution was washed with 2×150 mL of 0.5M aqueous sodium bisulfate and 200 mL of brine.

The solution was then concentrated in vacuo to a pale amber oil which was redissolved in 50 mL of diethyl ether. Hydrogen peroxide (30%, 15 mL) was added followed by sufficient absolute ethanol to obtain a homogeneous solution (ca. 50 mL). After stirring at 20° C. for 14 h, the mixture was concentrated in vacuo without warming (bath temperature ≦20° C.) to ca. 20% volume to remove the majority of the solvents. Ethyl acetate:hexane (1:1, 200 mL) was added and the solution washed with 100 mL of water and 100 mL of saturated aqueous sodium bicarbonate. An emulsion formed which was broken up by addition of 200 mL of brine followed by extraction with 2×500 mL of ethyl acetate:hexane (1:1). The combined extracts were washed with 300 mL of brine and dried over anhydrous sodium sulfate. Concentration in vacuo (≦20° C.) afforded 5.2 g of a colorless resin. The mixture was flash chromatographed on 400 g of silica gel eluting with a gradient of 4% ethyl acetate in dichloromethane:hexanes (40:60) to 6% ethyl acetate in dichloromethane:hexanes (60:40) over ca. 4 L. First eluted was unreacted excess imide followed by 4.43 g (81%) of the desired aldol product as a nearly colorless resin. This material is somewhat unstable and should be used immediately in the azide displacement reaction.

Mass spectrum (field desorption ionization) m/e=535 (M+), 455 (−HBr).

$^1$H NMR ($CDCl_3$, 300 MHz) δ7.195-7.374 (m, 5, Ph) 5.891 (dt, 1, J=15.5, 6.6 Hz, CHCH═) 5.677 (d, 1, J=5.3 Hz, CHBr) 5.487 (dd, 1, J=15.5, 6.6 Hz, $CH_2CH$═), 4.723 (m, 1, NCH) 4.680 (dt, 1, J=5.3 Hz, CH—OH) 4.270 (d, 2, J=7.3 Hz, $CH_2O$) 3.295 (dd, 1, J=13.4, 3.3 Hz, $CH_2Ph$), 2.807 (dd, 1, J=13.4, 9.4 Hz, $CH_2Ph$) 2.030 (dd, 2, J=13.8, 6.8 Hz, $CH_2CH$═) 1.24-1.38 (m, 22, $CH_2$) 0.872 (t, 3, J=6 Hz $CH_3$).

EXAMPLE 3

(S)-3-(Trans-2-azido-3-hydroxy-4-octadecenoyl-4-benzyl-2-oxazolidinone from
(S)-4-Benzyl-3-(trans-2-bromo-3-hydroxy-4-octadecenoyl)-2-oxazolidinone To 536 mg (1.00 mmol) of bromoaldol compound in 10 mL of dry dimethyl sulfoxide was added 130 mg (2.00 mmol) of sodium azide, and the reaction mixture was stirred at 20° C. After 18 h, the DMSO was evaporated without warming at high vacuum ($10^{-3}$ Torr), and the residue was treated with 120 mL of water and extracted three times with 100 mL of ethyl acetate:hexane, 1:1. The combined organic layer was washed with 50 mL brine and dried over anhydrous sodium sulfate. Concentration in vacuo afforded an oil which, according to the $^1$H NMR spectrum, contained a 9:1 mixture of azide epimers.

Flash chromatography on 80 g of silica gel with 20% ethyl acetate:hexane gave 418 mg (84%) of the pure desired azide epimer as an oil (Rf 0.33, 25% ethyl acetate:hexane). Next eluted was 43 mg (9%) of the minor azide epimer (Ref 0.20). $^1$H NMR spectral data of both products were identical to materials produced from the corresponding chloro derivative ((S)-4-benzyl-3-(trans-2-chloro-3-hydroxy-4-octadecenoyl-2-oxazolidinone.)

The invention has been described in detail with particular reference to preferred embodiments thereof, but it will be understood that variations and modifications can be effected within the spirit and scope of the invention.

What is claimed is:

1. A compound having the following formula:

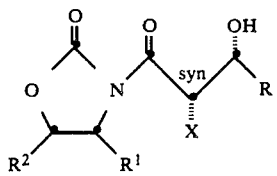

wherein R is alkyl having 6-12 carbon atoms, alkenyl having from 2 to 22 carbon atoms or aryl having 6-25 carbon atoms, $R^1$ is benzyl, $R^2$ is hydrogen or alkyl having from 1-10 carbon atoms, and X is a halogen atom.

2. A compound having the following formula:

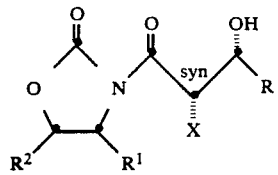

wherein R is alkyl having from 6-12 carbon atoms, alkenyl having from 2 to 22 carbon atoms or aryl having 6-25 carbon atoms, $R^1$ is benzyl; $R^2$ is hydrogen; and X is a halogen atom.

3. The compound of claim 2 wherein X is chlorine or bromine.

4. The compound of claim 2 wherein R is alkenyl.

5. The compound of claim 3 wherein R is $CH_2=CH-CH_3$.

6. The compound of claim 3 wherein R is $CH_2=CH(CH_2)_{12}CH_3$.

7. The compound of claim 2 wherein R is phenyl.

* * * * *